United States Patent [19]
Cassidy

[11] Patent Number: 6,117,076
[45] Date of Patent: Sep. 12, 2000

[54] PATIENT MONITORING SYSTEM AND METHOD

[75] Inventor: David Cassidy, Chelmsford, Mass.

[73] Assignee: Belmont Instruments Corporation, Billerica, Mass.

[21] Appl. No.: 09/157,762

[22] Filed: Sep. 21, 1998

[51] Int. Cl.$^7$ .................................. A61B 5/00; A61B 5/04
[52] U.S. Cl. ............................................ 600/300; 600/508
[58] Field of Search .................................... 600/508, 509, 600/300, 342, 478; 128/904

[56] References Cited

U.S. PATENT DOCUMENTS

| | | | |
|---|---|---|---|
| 4,694,837 | 9/1987 | Blakeley et al. | 128/653 |
| 4,742,831 | 5/1988 | Silvian | 600/509 |
| 5,307,817 | 5/1994 | Guggenbuhl et al. | 600/508 |
| 5,311,873 | 5/1994 | Savard et al. | 600/508 |

FOREIGN PATENT DOCUMENTS

| | | | |
|---|---|---|---|
| 59172-A1 | 9/1982 | European Pat. Off. | 600/509 |

OTHER PUBLICATIONS

Schematic, ECG & Pressure Amp, Belmont Instrument Corp, Drawing No. DPBP–444, (three sheets) 1992–1998.
"The Bard® TransAct™ System for Aortic Counterpulsation Therapy H–800 Intra–Aortic Balloon Pump" Service Manual, ©1993, V.1–V.3.
"Transformer Coupled Isolation Amplifier", Linear Products, Burr–Brown ®, ©1996, pp. 5.290–5.292, 5.295–5.296 5.300–5.304.
Spire Laser Power Converter Data Sheet.

*Primary Examiner*—Carl H. Layno
*Attorney, Agent, or Firm*—Cesari amd McKenna, LLP

[57] ABSTRACT

A system for monitoring an anatomical condition of a patient is provided. One embodiment of the system includes an electronic monitoring device for monitoring the anatomical condition (e.g., cardiac function) of the patient and for generating an electrical signal indicative of that monitored condition. The system converts the electrical signal into an optical signal that is indicative of the monitored condition, and supplies the optical signal via a fiber optic link to a remote location for processing. The system also supplies to the electronic monitoring device another optical signal via another fiber optic link. The other optical signal is for use both in controlling operation of and powering the electronic monitoring device.

13 Claims, 2 Drawing Sheets

PATIENT MONITORING SYSTEM AND METHOD

BACKGROUND OF THE INVENTION

1. Field of the Invention

The present invention relates generally to a patient monitoring system and method. More specifically, it relates to such a system and method that exhibit improved reliability and accuracy in electromagnetically noisy environments (e.g., environments in which significant amounts of ambient electromagnetic energy are present) compared to the prior art. Although the present invention finds particular utility in the area of monitoring a patient's cardiac function while the patient is undergoing electro-cautery surgery, other uses are also contemplated for the present invention, including monitoring of other anatomical conditions (e.g., brain electrical activity, respiratory function, etc.) and/or in other electromagnetically noisy environments.

2. Brief Description of Related Prior Art

Many conventional systems exist for monitoring patient anatomical and biological functions. For example, systems exist that can monitor a patient's heart and lung activities. One example of a conventional heart activity monitor is the electrocardiograph (ECG), which utilizes sensors placed on the patient's chest to generate electrical signals indicative of the patient's heart activity. These signals are carried by conductive wires or leads to a high gain electronic amplifier block that amplifies the signals from the sensors. The amplified electrical signals are then carried by additional electrically conductive wires to a remote signal processing system, such as a computer display system and/or other type of device (e.g., a printer) for providing to medical personnel a visual depiction of the monitored heart activity. Digital signal processing equipment may also be provided at the remote processing system to determine whether, and provide warning to medical personnel if, the monitored heart activity exceeds or falls below maximum and minimum safe thresholds, respectively, therefor. Also, in such patient monitoring devices, electrical isolation devices (e.g., a coupling transformer, miniature optocoupler system, etc.) are provided to protect the monitored patients from hazardous electrical shocks from the devices.

Typically, if a patient is undergoing certain types of medical and surgical procedures, it is desirable to monitor simultaneously the patient's heart and/or lung activities. These types of medical procedures include procedures making use of high energy equipment, which can generate magnetic fields and other types of electromagnetic interference. Such interference can induce stray currents in the connection wires and in the amplifier block itself, as a result of relatively large capacitances generated in the conducting wires and across the amplifier's isolation boundary (e.g., provided by the transformer coupling, miniaturized optocoupling, etc. used to provide shock protection to the patient). This injects noise into the signals being transmitted from the amplifier block to the remote processing system by providing a return path to ground via the capacitance between the amplifier block and the remote processing system. This reduces the reliability and accuracy of such monitoring equipment.

For example, in certain types of invasive medical procedures, an electrocautery device is used to carry out tissue cutting and coagulation operations. More specifically, such electrocautery devices may be used to generate high voltage, high frequency (e.g., radio frequency) electrical energy that may be applied to the patient to cut tissue or cauterize blood vessels. For the reasons discussed above, if an ECG is being used to monitor patient cardiac activity when this electrical energy is generated, electrical interference noise can be injected into the signals transmitted from the amplifier block to the remote processing system. This injected noise can distort the signals from the amplifier block to such a degree that they no longer accurately indicate monitored heart activity. As can be readily appreciated, this significantly reduces the accuracy and reliability of such conventional monitoring equipment. Thus, it would be desirable to provide a patient monitoring system that does not suffer from these disadvantages and drawbacks.

It would also be desirable to provide a control system that can be actuated remotely from the patient (e.g., at the remote processing system) to generate signals for controlling operation of the ECG, and that is designed to substantially prevent injection of noise into the control signals from ambient electromagnetic interference. As can be appreciated, unless such noise is substantially prevented from influencing the control signals generated by the control system, the control signals actually supplied to ECG may not accurately indicate the commands that are intended to be provided to the ECG.

SUMMARY OF THE INVENTION

In accordance with the present invention, a patient monitoring system and method are provided that overcome the aforesaid and other disadvantages and drawbacks of the prior art. More specifically, in the present invention, a patient monitoring system and method are provided which utilize respective, non-conducting fiber optic links to transmit signals indicative of the patient's anatomical condition being monitored, and signals for controlling operation of the ECG monitoring equipment. These non-conducting fiber optic links physically separate and electrically isolate conducting boundaries of the amplifier and remote processing systems such that there is a significant reduction in the capacitance generated between these systems compared to the prior art. By using these non-conducting fiber optic links in the present invention, it is possible to significantly reduce (e.g., by several orders of magnitude) the aforedescribed type of parasitic capacitance that may be influenced by ambient electromagnetic energy. Advantageously, this permits the system and method of the present invention to be substantially immune to the aforesaid deleterious effects of ambient electromagnetic energy.

In one embodiment of the system of the present invention, a first optical fiber link is provided to transmit first optical signals to a location remote from an electronic monitoring device. The first optical signals are indicative of a patient anatomical condition being monitored by the monitoring device. A second optical fiber link is also provided to transmit to the location of the monitoring device second optical signals, originating at the remote location, for use in controlling operation of the monitoring device.

These and other features and advantages of the present invention will be become apparent as the following Detailed Description proceeds and upon reference to the drawings wherein like numerals depict like parts, and in which:

Although the following Detailed Description will proceed with reference being made to illustrative embodiments and methods of use, it should be understood by those skilled in the art that the present invention is not intended to be limited to these embodiments and methods of use. Rather, the present invention should be viewed quite broadly as being limited only as set forth in the hereinafter appended claims.

DETAILED DESCRIPTION OF AN ILLUSTRATIVE EMBODIMENT

Figure 1:
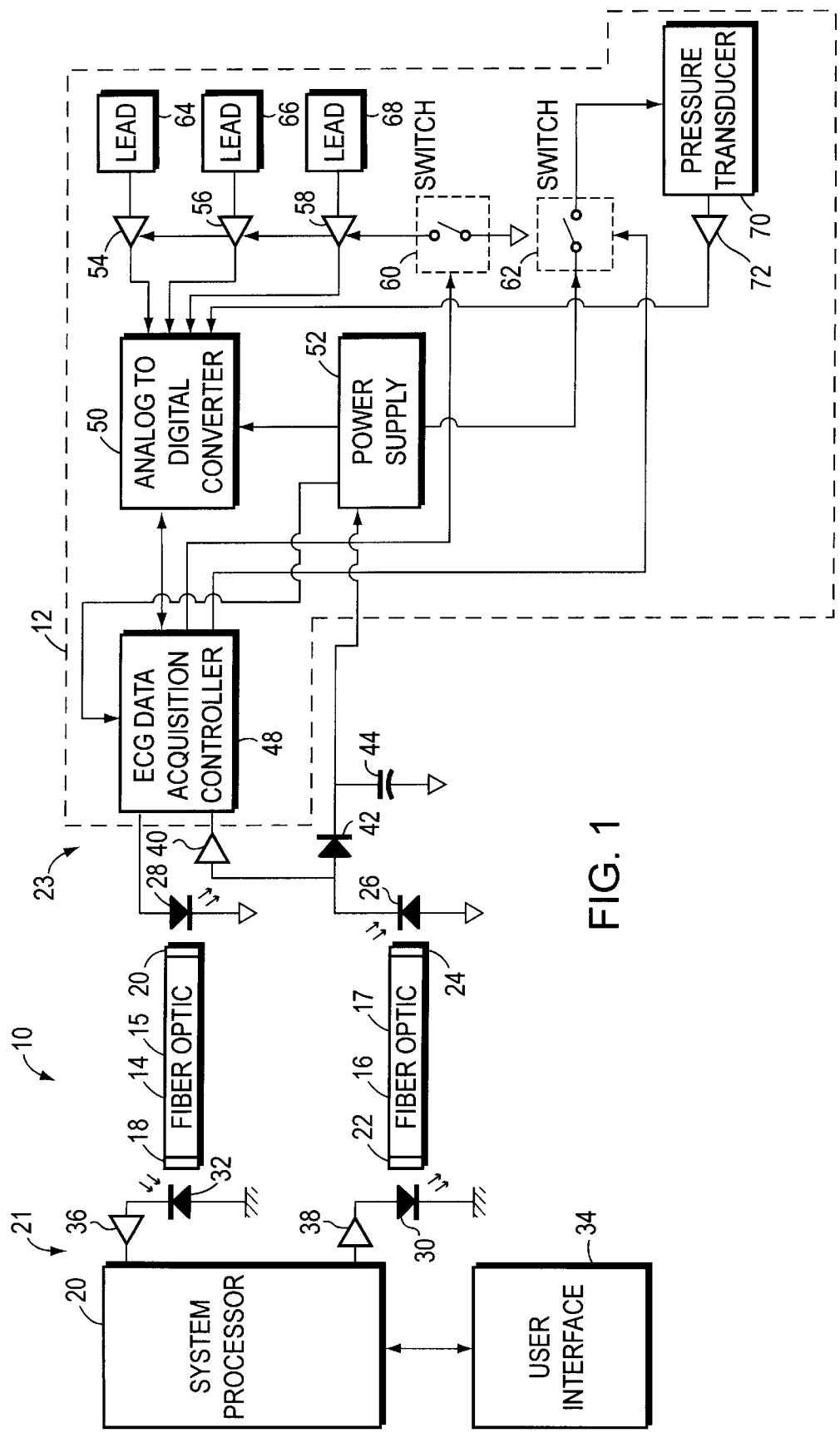
FIG. 1 is a highly schematic diagram of one preferred embodiment of system of the present invention.

FIG. 1 is a highly schematic diagram of one preferred embodiment 10 of the patient monitoring system of the present invention. System 10 includes an ECG and arterial pressure (AP) monitoring device 12 that is connected to, but electrically insulated from, a remote processor 20 by electrically non-conducting fiber optic-based links 15, 17. Device 12 includes a plurality of electrode leads 64, 66, 68 and an AP transducer 70 that are attached by conventional means (e.g., adhesive tape, not shown) to the chest of a patient so as to permit the heart activity (i.e., ECG waveform and arterial blood pressure) of the patient to be monitored by the monitoring device 12.

Each lead 64, 66, 68 is connected to the input of a respective amplifier 54, 56, 58. The outputs of the amplifiers 54, 56, 58 are connected to respective input channels of analog-to-digital converter (ADC) 50. The output of the transducer 70 is connected to the input of amplifier 72. The output of amplifier 72 is provided to another respective input channel of ADC 50.

Amplifiers 54, 56, 58, 72 provide to the respective input channels of the ADC 50 analog signals that are indicative of the status of the monitored anatomical condition (in this case, cardiac function) of the patient to which the leads 64, 66, 68 and transducer 70 are attached. ADC 50 samples and holds the analog signals supplied to its input channels so as to convert them into digital signals representative of the patient's heart activity. These digital signals are supplied to the ECG Data Acquisition Controller 48.

As will be described in greater detail, controller 48 encodes the digital signals provided to it by the ADC 50, and supplies the encoded digital signals to photo-electric converter device 28. Controller 48 also supplies control signals to ADC 50 and controllable switches 60, 62 to control operation of the ADC 50, and the states of the switches 60, 62 (i.e., whether the switches 60, 62 are opened or closed), respectively.

Power supply system 52 is coupled, and supplies appropriate actuating power (i.e., voltage and current) to, each of the ADC 50, controller 48, and transducer 70. However, in the case of transducer 70, supply of actuating power from the supply 52 is controlled by the state of the switch 62. That is, when the switch 62 is closed, actuating power is supplied from supply 52 to the pressure transducer 70, while when switch 62 is open, such actuating power is not supplied to the transducer 70. Switch 60 is coupled to both a "floating" (i.e., non-earth) ground potential and respective reset inputs of the amplifiers 54, 56, 58 such that when switch 60 is momentarily closed and thereafter reopened, a reset signal is supplied to each of the amplifiers 54, 56, 58 that causes these amplifiers 54, 56, 58 to reset their internal states to predetermined initialization states (i.e., the states that the amplifiers 54, 56, 58 are configured to enter immediately upon being powered-up after being powered-down).

Electrical power supplied by the power supply system 52 to power the monitoring device 12 is transmitted from the remote system 20 to the system 52 via the link 17. More specifically, laser light generated by a laser light emitting diode 30 is transmitted via link 17 to a photo-electric converter circuit comprising light-to-voltage converter 26, amplifier 40, and a voltage regulating circuit comprising diode 42 and "holdup" capacitor 44 (e.g., having a capacitance of 100 microfarads). The photo-electric converter 26 converts the laser light received via link 17 into electric power and control signals. Power supply system 52 comprises conventional circuitry (e.g., DC level converting and power distribution circuitry, etc.) for converting the electric power signals received from the photo-electric converter circuit 26 into signals of appropriate voltage and current levels to power the components 48, 50, 70. The electric control signals are supplied to the ECG controller 48 for controlling operation of the controller 48. Additionally, although not shown in the Figures for purposes of simplicity of illustration, amplifiers 54, 56, 58, 72 are also powered by the supply 52.

Converter 26 comprises a two-terminal laser power converter cell. One of the terminals of converter 26 is connected to the "floating" ground potential, and the other terminal is connected, in parallel, to the input of amplifier 40 and the anode of diode 42. The cathode of diode 42 is connected to the positive terminal of capacitor 44, and the negative terminal of the capacitor 44 is connected to the floating ground potential. The positive terminal of the capacitor 44 is also connected to the power supply 52. The output of amplifier 40 is connected to a data input line of the controller 48.

Converter 26 is coupled via conventional optical coupler means 24 to one end of fiber optical cable 16; the opposite end of cable 16 is coupled, via another conventional optical coupler means 22 to a laser light emitting diode 30 so as to permit laser light emitted by the diode 30 to be transmitted via the cable 16 and coupler 24 to cell 26. The cathode of the diode 30 is coupled to earth ground, while the anode of the diode 30 is coupled to the output of buffer 38. The input of buffer 38 is coupled to a signal output line of processor 20. Processor 20 supplies, via the buffer 38, electric signals to the diode 30 which are used to power and control operation of the monitoring device 12. The diode 30 is excited by these electric signals to generate laser light signals, which are supplied via link 17 to receiving light-to-voltage converter 26, that are representative of the electric signals from the processor 20.

Converter 28 comprises a light emitting diode whose anode is connected to the controller 48 so as to receive the encoded data signals from the controller 48. The cathode of the diode 28 is connected to the floating ground potential. Diode 28 generates light signals representative of the encoded data signals supplied thereto from the controller 48. Diode 28 is coupled to conventional optical coupling means 20 that permits the light signals generated by the diode 28 to be transmitted to the fiber optic cable 14, and thence, via another conventional optical coupling means 18 to receiving photo-electric converter 32.

Converter 32 comprises a photodiode whose anode is connected to earth ground and whose cathode is connected to the input of an amplifier 36. Diode 32 converts the light signals received from the link 15 into the encoded digital signals supplied to the diode 28 by the controller 48. These encoded digital signals are amplified by the amplifier 36, and the amplified signals are supplied to the processor 20.

A conventional user interface 34 is also provided in system 10, which interface 34 is coupled to the processor 20. Interface 34 may comprise a conventional personal computer system (e.g., an IBM-type, Intel 80X86-based personal computer system) that is configured to receive, store, and display (e.g., via a conventional graphical user interface) data supplied by the processor 20, and is also adapted to permit user input of commands to the processor 20 (e.g., via said graphical user interface). Although not shown in the Figures, the processor 20 and interface 34 are powered by a conventional user-actuable power supply (not shown) that is different from the power supply 52 used to power the monitoring device 12.

Preferably, in system 10, the processor 20, interface 34, amplifier 36, buffer 38, and converters 30, 32 are all located at a location 21 that is remote from the location 23 of the monitoring device 12, converters 26, 28, amplifier 40, diode 42 and capacitor 44. Also preferably, each of the amplifiers 40, 54, 56, 58, 72 comprises one or more respective operational amplifiers (e.g., of the type having part number LMC 6464 manufactured by National Semiconductor Corporation of Santa Clara, Calif.) configured to amplify the respective signals input to them. The ADC 50 may comprise a MAX147 integrated circuit chip manufactured by Maxim Integrated Products Inc. of Sunnyvale, Calif. Controller 48 may comprise a 16LC84 integrated circuit chip available from Microchip Technology, Inc. of Chandler, Ariz., and associated program/data RAM and ROM memory. Likewise, the remote processor 20 may comprise a 68HC16 integrated circuit chip available from Motorola, Inc. of Phoenix, Ariz. and associated program/data RAM and ROM memory. Buffer 38 may comprise an S16433 integrated circuit chip manufactured by Siliconix, Inc. of Santa Clara, Calif., and amplifier 36 may comprise an SFH551 integrated circuit chip available from Siemens, AG, of Munich, Germany. The pressure transducer amplifier 72 may be of a type manufactured by Analog Devices, Inc. of Norwood, Mass. Converter 26 may comprise a laser power converter, designed to convert specific wavelengths of laser light (e.g., wavelength bands in the red or infrared areas of the spectrum) into electrical energy, of a type manufactured by Spire Corporation of Bedford, Mass.

In operation of system 10, the leads 64, 66, 68 and transducer 70 are secured to the patient's chest so as to permit the monitoring device 12 to monitor the patient's cardiac activity. Thereafter, the processor 20 and interface 34 are powered-up (e.g., via user activation of the power supply that powers processor 20 and interface 34). After the processor 20 and user interface 34 have been properly powered-up and initialized, in order to start monitoring the patient's cardiac function, a user (not shown) enters appropriate commands via the interface 34 for causing the system 10 to initiate such monitoring. These commands are transmitted to the processor 20, which in response thereto, generates pulse code modulated (PCM) electric signals which are supplied to buffer 38. The electric signals that are supplied from the processor 20 to the buffer 38 control various aspects of the operation of the monitoring device 12, including whether the monitoring device 12 is powered-up or powered-down, and other aspects of said operation. In the following discussion, the electrical signals that are supplied from the processor 20 to the buffer 38 will be referred to as "electrical power and control signals."

Buffer 38 is configured to electrically isolate the circuits of the processor 20 from the laser light emitting diode 30, and maintains the voltage level of the signals input to buffer 38 from the processor 20 while "boosting" (i.e., substantially increasing) the current level of those signals. That is, the signals output by the buffer 38 to the laser light emitting diode 30 are at the same respective voltage levels as the corresponding signals input to the buffer 38, but the signals output by the buffer 38 have a substantially greater current level than those corresponding signals. The output signals from the buffer 38 are then supplied to the laser light emitting diode 30.

Diode 30 converts the "boosted" power and control signals supplied thereto from the buffer 38 into laser light whose amplitude and power levels are related to the boosted power and control signals. These optical power and control signals are then transmitted by the link 17 to the light-to-voltage converter 26. The converter 26 recovers from the optical power and control signals the boosted electrical power and control signals from which they were generated, which recovered signals are then supplied in parallel to the amplifier 40 and diode 42. Diode 42 is biased so as to permit the reconverted signals to propagate to the power supply 52 and to capacitor 44, but to prevent signal propagation from these components 44, 52 to the diode 26 and amplifier 40.

As stated previously, the signals supplied to the buffer 38 from the processor 20 are PCM signals. In the PCM encoding scheme, digital signal pulses of relatively longer or shorter durations are interpreted as data bits of different logic levels. For example, a data bit of logic "1" is encoded by a signal pulse (e.g., 2 microseconds) of relatively long duration, while a data bit of logic "0" is encoded by a pulse (e.g., 1 microsecond) of relatively shorter duration. Thus, since in system 10, the power and control signals are PCM signals, there will be intermittent periods wherein the reconverted power and control signals will have zero amplitude. During these intermittent periods, charge previously stored in the capacitor 44 is discharged therefrom and supplied to the supply 52 for use in powering the monitoring device 12. Conversely, in between these intermittent periods, the capacitor 44 is charged by the recovered power and control signals. The electric energy supplied to the supply 52 from the cell 26 and capacitor 44 is converted by the conventional circuitry of the supply 52 into respective voltage and current levels appropriate for powering the various components of the monitoring device 12, and are supplied to these components whereby to power-up the monitoring device 12.

Controller 48 is programmed such that, after the controller 48 has powered-up and initialized its internal registers, etc., controller 48 waits a predetermined time period (e.g., at least about 2.5 milliseconds) that has been empirically determined to be sufficient for the ADC 50 and amplifiers 54, 56, 58, 72 to stabilize after initial power-up, and thereafter, provides a data synchronization clock signal to ADC 50 to permit the controller 48 and ADC 50 to be able to exchange data and commands. In response, the ADC 50 provides to the controller 48 an acknowledgment signal that indicates that the ADC 50 is now ready, when commanded by the controller 48, to begin digitizing signals received from the amplifiers 54, 56, 58 and 72, and to supply the resulting digital signals to the controller 48.

In response to receipt of the acknowledgment signal from the ADC 50, the controller 48 generates PCM encoded, ready signals that indicate that the monitoring device 12 is now ready to begin monitoring the patient's cardiac functioning, and provides the encoded ready signal to the light emitting diode 28. The encoded electric ready signals supplied to the diode 28 provide sufficient excitation energy to the diode 28 to cause the diode 28 to generate PCM light signals, corresponding to the PCM encoded, electric ready signals. These PCM light signals are transmitted via link 15 to receiving photodiode 32. Photodiode 32 recovers from the PCM light signals that it receives the PCM electric ready signals, which ready signals are then amplified by amplifier 36 (e.g., to compensate for signal attenuation from processing by diodes 28, 32 and propagation through link 15) and are supplied to the processor 20.

Processor 20 decodes the PCM ready signals to generate a bit stream that is interpreted by the processor 20 as indicating that the monitoring device 12 is now ready to begin monitoring the patient's cardiac function. The processor 20 then supplies appropriate commands to the interface 34 to cause the interface 34 to indicate to the user that system 10 is now ready to begin monitoring the patient's cardiac function, and to prompt the user to inform the system 10 as to the manner in which monitoring of the cardiac function is to be carried out by the system 10.

For example, the user prompt provided by the interface 34 may request that the user provide commands via the interface 34 specifying which of the input channels of the ADC 50 are to be used to measure cardiac function, desired frequency of such measurements and measurements of patient AP, etc. Additionally, the interface 34 may also permit the user to command that the amplifiers 54, 56, 58 be reset, and/or to specify other commands.

The commands input by the user via the interface 34 to the system 10 are received by the processor 20. In response to receipt of these commands, the processor 20 generates and supplies to the buffer 38 PCM power and control signals which may be decoded to recover these commands. These power and control signals are then processed by the buffer 38, diode 30, link 17, and cell 26 in the aforedescribed manner.

The impedance of the circuit branch consisting of the diode 42, capacitor 44 and power supply 52, and the impedance of the circuit branch consisting of the amplifier 40 and controller 48 are selected such that the power of the PCM signals transmitted from the converter 26 is split between these two branches in such a way that the power delivered to the latter circuit branch is several orders of magnitude less than that delivered to the former circuit branch. This permits the vast majority of power of the recovered power and control signals to be used to power the monitoring device 12, and prevents the controller 48 from becoming overloaded with excessive power from these PCM signals. Given the significantly reduced strength of the power and control signals provided to the latter branch, amplifier 40 is provided to permit same to be usable as control signals for controlling operation of the controller 48.

The controller 48 decodes PCM signals provided to it to reconstruct the commands that the processor 20 wishes the controller 48 to execute. After the controller 48 determines these commands, the controller 48 provides appropriate control signals to the ADC 50 and/or switches 60, 62 to carry out said commands, and after carrying them out, the controller 48 provides appropriate PCM acknowledgment signals to the processor 20 (via the diode 28, link 15, diode 32, and amplifier 36) to indicate that these commands have been carried out.

For example, the commands provided to the controller 48 from the processor 20 may indicate that all of the input channels of the ADC 50 are to be used in monitoring the patient's cardiac function, and that measurements of heart activity and AP are to be made by the monitoring device 12 using a default measurement cycle (e.g., readings of heart activity measured via the leads 64, 66, 68 are to be taken every 1.25 milliseconds, and AP readings are to be taken every 10 milliseconds) that is preprogrammed into the controller 48. If such a default measurement cycle is commanded, the measurement process implemented by the controller 48 is as illustrated in FIG. 2.

Figure 2:
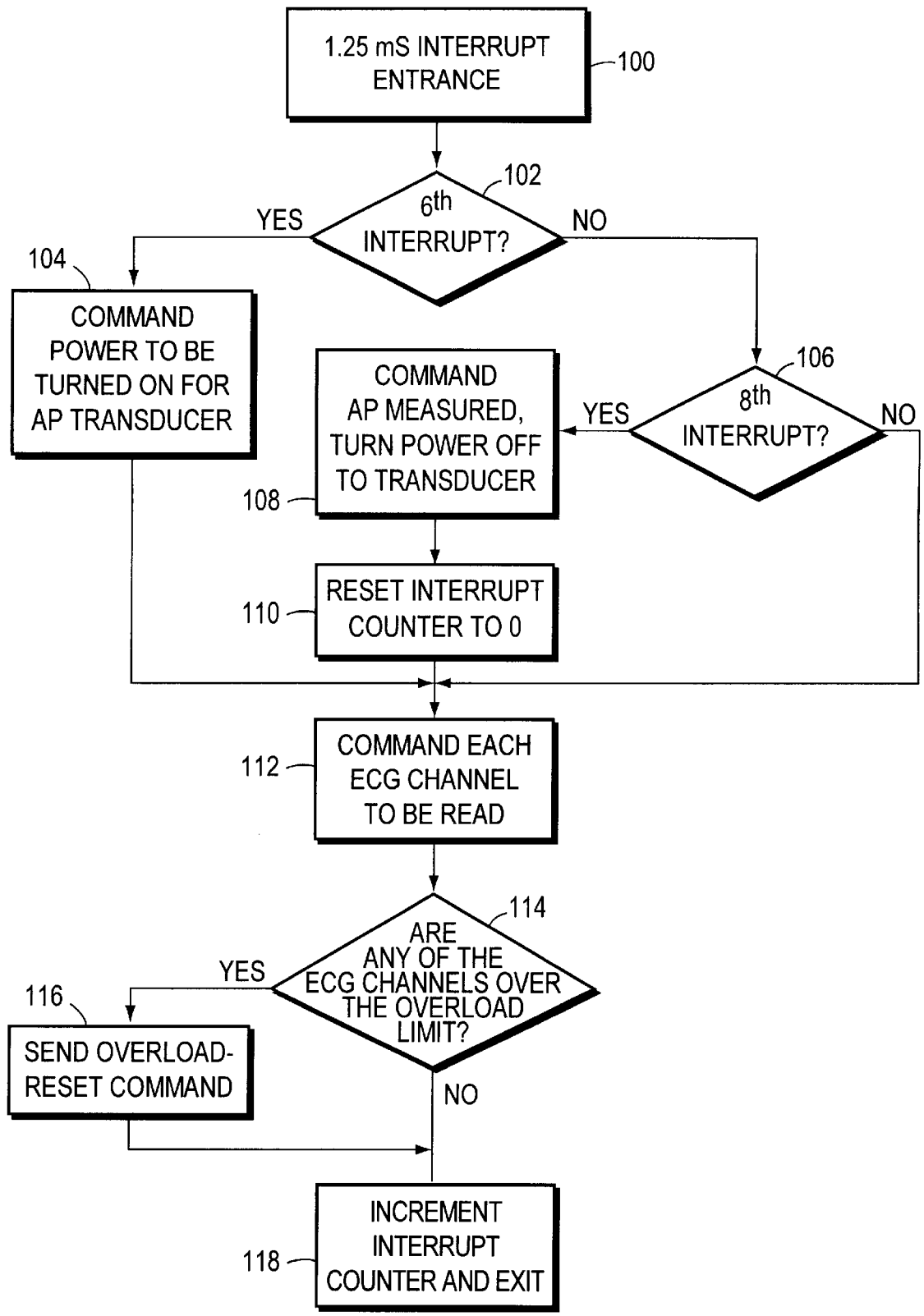
FIG. 2 is a flowchart for use in describing the operation of the system of FIG. 1.

As shown in FIG. 2, in the default measurement cycle, the controller 48 generates measurement cycle interrupts every 1.25 milliseconds which trigger an interrupt processing routine whose execution begins, as shown, at block 100. After beginning execution of the routine, the controller 48 determines whether an interrupt counter variable (which is initialized to zero when the controller 48 powers up) is equal to six (see block 102), and if so, the controller 48 supplies a control signal to the switch 62 that causes the switch 62 to close so that power is supplied from supply 52 to the transducer 70 (see block 104). Prior to supply of this control signal, the transducer 70 is powered-down so as to minimize energy drain on supply 52.

After causing the transducer 70 to be powered-up, the controller 48 commands all of the channels of the ADC 50 to be sampled and the signals being input thereto from the amplifiers 54, 56, 58 to be digitized (see block 112). These digitized signals are then supplied to the controller 48, which provides them, in the aforedescribed manner, as pulse code modulated signals, to the processor 20. The processor 20 decodes the pulse code modulated signals to recover the digitized signals, and determines whether they are outside a predetermined range of expected values therefor that has been empirically determined to be indicative of normal operation of the monitoring device 12 (i.e., if any of the values of the digitized signals is outside of this range, the processor 20 determines that a failure condition, such as saturation of one of the amplifiers 54, 56, 58, has occurred in the monitoring device 12; see block 114). If such a failure condition is determined to exist, the processor 20 transmits appropriate PCM signals to the controller 48 to remedy the situation by causing the controller 48 to control the reset switch 60 to provide the reset signal to the amplifiers 54, 56, 58. Likewise, if the processor 20 does not receive within a predetermined "time out" period after the transmission of the reset command to the controller 48 an appropriate acknowledgment signal from the controller 48 that indicates that the controller 48 has carried out the reset command, the processor 20 determines that an ECG "lockup" failure condition is present, and remedies this by temporarily ceasing provision of power and control signals to the monitoring device 12 so as to temporarily power-down, and thereafter, power-up the ECG12 into the ECG's initial power-up state. Otherwise, if the processor 20 does not take action to remedy presence of a failure condition in the monitoring device 12, the controller's interrupt routine terminates after incrementing the interrupt counter variable.

Alternatively, if at block 102, controller 48 determines that the interrupt counter variable is not equal to six, the controller 48 determines whether the interrupt counter variable is equal to eight (see block 106). If at block 106, the counter variable is not equal to eight, the interrupt process branches to block 112.

Otherwise, if at block 106, the counter variable is equal to eight, the controller 48 supplies control signals to the ADC 50 to digitize the AP signal being supplied from the amplifier 72, and to supply this digitized AP signal to the controller 48. The controller then opens the switch 62, thereby deactivating the transducer 70, and resets the interrupt counter variable to zero (see blocks 108 and 110). The controller 48 then encodes the digitized AP signal supplied from the ADC 50 into PCM signal format, and supplies this PCM AP data signal to the processor 20.

Data values (i.e., representing cardiac activity and AP), decoded by the processor 20 from the PCM data signals sent from the monitoring device 12, are processed by the processor 20 to put them into a format suitable for processing by the interface 34 (e.g., for display via the graphical user interface of the interface 34). These processed signals are then supplied to the interface 34, which generates therefrom a user-appreciable display of the measurements of the patient's cardiac function taken using the monitoring device 12 and/or undertakes additional conventional processing.

As will be appreciated by those skilled in the art, the value to which the interrupt counter variable is compared at blocks 102 and 106, and the frequency of measurement interrupts, may be provided to the controller 48 by the PCM signals from the processor 20. Thus, by appropriately selecting this value and the frequency of measurement interrupts, any arbitrary measurement rate of heart activity and AP may be commanded by the processor 20 to be implemented by the monitoring device 12.

Additionally, controller 48 may comprise non-volatile memory storing preprogramed calibration constants related to operation of the amplifiers 54, 56, 58, 72. These calibration constants may be provided, upon initial power-up of the monitoring device 12, to the processor 20 to permit the processor 20 to appropriately adjust (i.e., normalize) data from the channels of the ADC 50 so as to compensate for differences in measurement data from those channels due to relative performance differences between the amplifiers 54, 56, 58, 72. For example, these calibration constants may include information that may be used by the processor 20 to appropriately adjust the measurements being received from the monitoring device 12 to account for changes in performance (e.g., gain characteristics, etc.) of the amplifiers 54, 56, 58, 72 that may result from aging of amplifiers 54, 56, 58, 72, ambient temperature changes, etc.

Preferably, the factor by which the output signals of the buffer 38 are boosted relative to the signals input to the buffer 38 is empirically determined so as to permit the portion of the reconverted power and control signals provided to supply 52 to be of sufficient average power to power the monitoring device 12 (e.g., about 30 mW). Also preferably, the size of capacitor 44 is chosen so as to permit the capacitor 44 to be able to store sufficient charge given the duty cycle of the PCM power and control signals to power the monitoring device 12 when the PCM power and control signals have zero amplitude.

Advantageously, it has been found that use of the fiber optic links in system 10 dramatically reduces (e.g., by several orders of magnitude) the parasitic capacitance generated in the system 10 compared to the prior art. More specifically, since the fiberopticbased links of system 10 are substantially non-conducting, this permits the system 10 to exhibit greatly improved resistance to noise injection to system 10 from ambient electromagnetic energy and improved patient isolation characteristic compared to prior art systems which implement patient isolation techniques based upon transformers and miniature optocouplers.

Thus, it is evident that there has been provided, in accordance with the present invention, a system and method for monitoring an anatomical condition of a patient that fully satisfy the aims and objectives hereinbefore set forth. As will be appreciated by those skilled in the art, many alternatives, modifications, and variations of the illustrative embodiments described above are possible without departing from the present invention.

For example, although the processor 20 has been described as providing electrical signals that both supply power to the monitoring device 12 and control operation of the monitoring device 12, if system 10 is appropriately modified, the power supply 52 may include appropriate conventional DC power supply means (e.g., batteries, etc.) for supplying power to the monitoring device 12 without requiring supply of power from the processor 20.

Additionally, if system 10 is appropriately modified, rather than being implemented by the controller 48, the measurement process of FIG. 2 may instead be implemented by the processor 20. More specifically, in this modification of system 10, the processor 20 may be programmed to carry out the measurement cycle interrupts and interrupt processing routine, previously described as being carried out by controller 48, based upon the user-input commands provided to the processor 20 via the interface 34. The processor 20 may issue electrical power and control signals to cause the controller 48 to appropriately control the switches 60, 62, ADC 50, etc. to carry out measurements of AP and ECG activity and to supply same to the processor 20, supply reset signals to amplifiers 54, 56, 58, etc., as needed, to carry out the processing at steps 104, 108, 112, and 116 of the interrupt service routine. Advantageously, this modification permits system 10 to exhibit greater design modularlity.

Other modifications are also possible. Accordingly, the present invention should be viewed as being of broad scope, and as being limited only as set forth in the hereinafter appended claims.

What is claimed is:

1. A patient monitoring system, comprising:
   a first optical fiber link for transmitting first optical signals to a location remote from of an electronic monitoring device, said first optical signals being indicative of a patient anatomical condition being monitored by said monitoring device; and
   a second optical fiber link for transmitting to said location of said monitoring device second optical signals originating at said remote location for use in controlling operation of said monitoring device, said second signals also being for use in supplying activation power to said monitoring device.

2. A patient monitoring system according to claim 1, wherein said condition comprises patient cardiac function.

3. A patient monitoring system according to claim 1, wherein said monitoring device generates analog electrical signals indicative of patient heart activity, and also comprises a digital encoding system for digitizing and encoding said analog electrical signals.

4. A patient monitoring system according to claim 3, wherein said digital encoding system comprises an analog-to-digital converter (ADC) for digitizing said analog signals, and a controller for encoding digital signals produced by said ADC from said analog signals.

5. A patient monitoring system according to claim 4, wherein second signals are for use in controlling said ADC.

6. A patient monitoring system according to claim 1, further comprising at said remote location, a processor configured to determine whether a failure condition is present in said patient monitoring system, and to cause a resetting of said monitoring device if said failure condition is determined by said processor to be present.

7. A patient monitoring system according to claim 3, wherein said monitoring device comprises an amplifier for amplifying said analog signals, and said second signals are also for use in powering said amplifier.

8. A patient monitoring system according to claim 1, wherein said monitoring device comprises a controller for controlling operation of said monitoring device, and said second signals are also for use in powering and controlling said controller.

9. A method for monitoring a patient anatomical condition, comprising:
   using an electronic monitoring device to generate an electric signal indicative of said condition;
   converting said electric signal into an optical signal;
   transmitting said optical signal via an optical fiber link to a location remote from said monitoring device; and
   supplying to said monitoring device another electric signal for both powering and controlling said monitoring device, said another electric signal being generated from another optical signal transmitted via another optical fiber link from said remote location.

10. A method according to claim 9, wherein a laser light signal is used as said another optical signal.

11. A method according to claim 9, wherein said monitoring device comprises a controller for controlling operation of the monitoring device and a power supply for providing power to the monitoring device, and said method further comprises providing portions of said another electric signal to said controller and said power supply.

12. A method according to claim 9, wherein said another optical signal is generated based upon a second electric signal generated by a processor at said remote location.

13. A method according to claim 12, further comprising, recovering the electrical signal that is indicative of the condition from the optical signal transmitted to the remote location, and providing the recovered electrical signal to the processor.

* * * * *